(12) United States Patent
Karrowni

(10) Patent No.: US 10,881,509 B2
(45) Date of Patent: Jan. 5, 2021

(54) TRANSCATHETER MITRAL VALVE PROSTHESIS

(71) Applicant: Kar Health, LLC, Cedar Rapids, IA (US)

(72) Inventor: Wassef Karrowni, Cedar Rapids, IA (US)

(73) Assignee: Kar Health, LLC, Cedar Rapids, IA (US)

( * ) Notice: Subject to any disclaimer, the term of this patent is extended or adjusted under 35 U.S.C. 154(b) by 114 days.

(21) Appl. No.: 16/047,626

(22) Filed: Jul. 27, 2018

(65) Prior Publication Data

US 2019/0029815 A1 Jan. 31, 2019

Related U.S. Application Data

(60) Provisional application No. 62/537,815, filed on Jul. 27, 2017.

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01); *A61F 2230/008* (2013.01); *A61F 2230/0019* (2013.01); *A61F 2250/0014* (2013.01); *A61F 2250/0039* (2013.01); *A61F 2250/0064* (2013.01); *A61F 2250/0069* (2013.01)

(58) Field of Classification Search
CPC ............. A61F 2/12; A61F 2/24; A61F 2/2418
USPC ....................................... 623/7–8, 1.24–1.26
See application file for complete search history.

(56) References Cited

U.S. PATENT DOCUMENTS

| | | | |
|---|---|---|---|
| 8,628,492 B2* | 1/2014 | Lin | A61F 9/00781 604/8 |
| 10,098,736 B2* | 10/2018 | Carmi | A61F 2/2442 |
| 10,245,142 B2* | 4/2019 | Bonhoeffer | A61F 2/2418 |
| 2006/0136045 A1* | 6/2006 | Flagle | A61B 17/00234 623/1.24 |
| 2009/0259292 A1* | 10/2009 | Bonhoeffer | A61F 2/2409 623/1.15 |
| 2010/0004635 A1* | 1/2010 | Lin | A61F 9/00781 604/540 |
| 2013/0304197 A1* | 11/2013 | Buchbinder | A61F 2/2418 623/2.11 |
| 2014/0200663 A1* | 7/2014 | Ferrari | A61F 2/2409 623/2.38 |
| 2014/0277408 A1* | 9/2014 | Folan | A61F 2/2412 623/2.11 |
| 2016/0302920 A1* | 10/2016 | Al-Jilaihawi | A61F 2/2433 |
| 2019/0216598 A1* | 7/2019 | Von Segesser | A61F 2/2427 |
| 2019/0343629 A1* | 11/2019 | Solem | A61F 2/2418 |
| 2020/0000593 A1* | 1/2020 | Besselink | A61F 2/2412 |

* cited by examiner

*Primary Examiner* — Suzette J Gherbi
(74) *Attorney, Agent, or Firm* — Davis, Brown, Koehn, Shors & Roberts, P.C.

(57) ABSTRACT

Disclosed herein are implantable dual-valve devices having first and second valve structures, a connector coupled to the structures, and first and second sealing members coupled on each side of the device, along with related methods of deploying such devices.

20 Claims, 4 Drawing Sheets

TRANSCATHETER MITRAL VALVE PROSTHESIS

CROSS-REFERENCE TO RELATED APPLICATION(S)

This application claims the benefit under 35 U.S.C. § 119(e) to U.S. Provisional Application 62/537,815, filed Jul. 27, 2017 and entitled "Transcatheter Mitral Valve Prosthesis," which is hereby incorporated herein by reference in its entirety.

FIELD OF THE INVENTION

The various embodiments herein relate to transcatheter valve replacement and artificial valves for use in such procedures.

BACKGROUND OF THE INVENTION

The mitral valve is a very complex three-dimensional structure in the human heart that separates the left atrium (upstream) from the left ventricle (downstream) and normally functions as a one-way valve. More specifically, the mitral valve allows blood to flow from the left atrium to the left ventricle during the diastole part of the cardiac cycle and to prevent blood flow backward from the left ventricle to the left atrium during the systole part of the cardiac cycle.

Mitral valve diseases, including stenosis (blockage of forward blood flow) and regurgitation (backward leakage of blood), are serious and common medical problems that arise, especially with age. The most common—and typically severe—symptom is shortness of breath, and the condition often leads to heart failure and death. Currently, the standard treatment is surgical repair or replacement of the valve. While this is an effective therapy, it is very invasive as it requires opening the patient's chest and in many cases, the patients are often too sick to survive such an operation. More recently, percutaneous transcatheter repair approaches have been developed. However, these are currently not an option for all patients.

Transcatheter valve replacement (using a valve prosthesis introduced via a minimally-invasive approach, such as through the femoral artery, for example) is a known method for treating aortic valve disease. Several different such replacement procedures are known. Further, minimally-invasive approaches for treating mitral valve disease are currently being developed. One example of such an approach is depicted in FIG. 1. This known procedure utilizes a known expandable artificial valve 10 that is deployed via a catheter 12. Each of these prostheses is typically composed of a metallic frame designed to fit in the annulus and provide radial strength in order to secure its position therein. Further, either bovine pericardial tissue or a porcine valve is sown over the frame to function as the valve leaflets. One disadvantage of these devices is that the implantable prosthesis has only one artificial circular valve, and thus doesn't fit well into the annulus where the prosthesis is implanted, which has a dynamic D-shaped structure. Another disadvantage is that the cylindrical shape of the known devices imposes a risk of obstruction of the outflow of the left ventricular heart chamber.

There is a need in the art for improved minimally-invasive transcatheter mitral valve therapeutic procedures and mitral valve prostheses for use in such procedures.

BRIEF SUMMARY OF THE INVENTION

Discussed herein are various implantable artificial valve structures and related methods for implanting the structures.

In Example 1, a dual-valve prosthesis comprises a first valve structure comprising a first valve disposed therein, a second valve structure comprising a second valve disposed therein, a connector coupled to the first and second valve structures, a first sealing member coupled to the first valve structure, the second valve structure, and the connector on a first side of the prosthesis, and a second sealing member coupled to the first valve structure, the second valve structure, and the connector on a second side of the prosthesis.

Example 2 relates to the dual-valve prosthesis according to Example 1, wherein the connector comprises a lumen defined therethrough.

Example 3 relates to the dual-valve prosthesis according to Example 1, wherein further comprising a third sealing member coupled to the first valve structure, the second valve structure, and the connector on the first side of the prosthesis, and a fourth sealing member coupled to the first valve structure, the second valve structure, and the connector on the second side of the prosthesis.

Example 4 relates to the dual-valve prosthesis according to Example 1, wherein the first valve structure is deployable between a first valve retracted position and a first valve deployed position.

Example 5 relates to the dual-valve prosthesis according to Example 4, wherein the second valve structure is deployable between a second valve retracted position and a second valve deployed position.

Example 6 relates to the dual-valve prosthesis according to Example 1, wherein the first valve comprises three first valve leaflets and the second valve comprises three second valve leaflets.

Example 7 relates to the dual-valve prosthesis according to Example 1, wherein the connector is fluidically sealed to the first and second valve structures, and wherein the first and second sealing members are fluidically sealed to the first valve structure, the second valve structure, and the connector.

Example 8 relates to the dual-valve prosthesis according to Example 1, wherein the first valve structure is a first expandable frame and the second valve structure is a second expandable frame.

Example 9 relates to the dual-valve prosthesis according to Example 1, wherein the first valve structure comprises a first rim at a first end of the first valve structure and a second rim at a second end of the first valve structure, and wherein the second valve structure comprises a third rim at a first end of the second valve structure and a fourth rim at a second end of the second valve structure.

In Example 10, a dual-valve prosthesis comprises a connector comprising a lumen defined therethrough, wherein the lumen extends along a length of the connector, a first expandable valve body coupled to a first side of the connector, the first valve body comprising a first valve disposed therein, a second expandable valve body coupled to a second side of the connector. the second valve body comprising a second valve disposed therein, a first sealing member coupled to the first valve body, the second valve body, and the connector on a first side of the prosthesis, and a second sealing member coupled to the first valve body, the second valve body, and the connector on a second side of the prosthesis.

Example 11 relates to the dual-valve prosthesis according to Example 10, further comprising a third sealing member coupled to the first valve body, the second valve body, and the connector on the first side of the prosthesis, wherein the third sealing member is disposed at a different axial location along the first side of the prosthesis in relation to the first sealing member, and a fourth sealing member coupled to the first valve body, the second valve body, and the connector on the second side of the prosthesis, wherein the fourth sealing member is disposed at a different axial location along the second side of the prosthesis in relation to the second sealing member.

Example 12 relates to the dual-valve prosthesis according to Example 10, wherein the first valve body is deployable between a first valve retracted position and a first valve expanded position and the second valve body is deployable between a second valve retracted position and a second valve expanded position.

Example 13 relates to the dual-valve prosthesis according to Example 10, wherein the first valve comprises three first valve leaflets and the second valve comprises three second valve leaflets.

Example 14 relates to the dual-valve prosthesis according to Example 10, wherein the connector is fluidically sealed to the first and second valve bodies, and wherein the first and second sealing members are fluidically sealed to the first valve body, the second valve body, and the connector.

Example 15 relates to the dual-valve prosthesis according to Example 10, wherein the first valve body is a first expandable frame and the second valve body is a second expandable frame.

Example 16 relates to the dual-valve prosthesis according to Example 10, wherein the first valve body comprises a first rim at a first end of the first valve body and a second rim at a second end of the first valve body, and wherein the second valve body comprises a third rim at a first end of the second valve body and a fourth rim at a second end of the second valve body.

In Example 17, a method of implanting a dual-valve prosthesis in a heart of a patient comprises positioning the prosthesis in the heart of the patient via a catheter, and deploying the prosthesis in an opening in a wall of the heart such that the prosthesis is fluidically sealed to the wall. The prosthesis comprises a first valve structure comprising a first valve disposed therein, a second valve structure comprising a second valve disposed therein, a connector coupled to the first and second valve structures, a first sealing member coupled to the first valve structure, the second valve structure, and the connector on a first side of the prosthesis, and a second sealing member coupled to the first valve structure, the second valve structure, and the connector on a second side of the prosthesis.

Example 18 relates to the method according to Example 17, wherein the deploying the prosthesis further comprises causing the first and second valve structures to expand to deployed configurations, thereby establishing a fluidic seal between the first and second valve structures and the wall.

Example 19 relates to the method according to Example 17 wherein the deploying the prosthesis further comprises positioning a deployment balloon device comprising first and second balloons such that the first balloon is disposed within the first valve structure and the second balloon is disposed within the second valve structure, and inflating the first and second balloons and thereby expanding the first and second valve structures into the deployed configurations.

Example 20 relates to the method according to Example 17, further comprising urging the prosthesis distally through the catheter and over a guidewire disposed through a lumen defined in the connector.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments herein relate to a mitral dual-valve prosthesis (also referred to herein as an "artificial implant," "artificial valve implant," "implant," or "valve implant") that can be delivered via a transcatheter approach to the heart, and related delivery methods.

Figure 1:
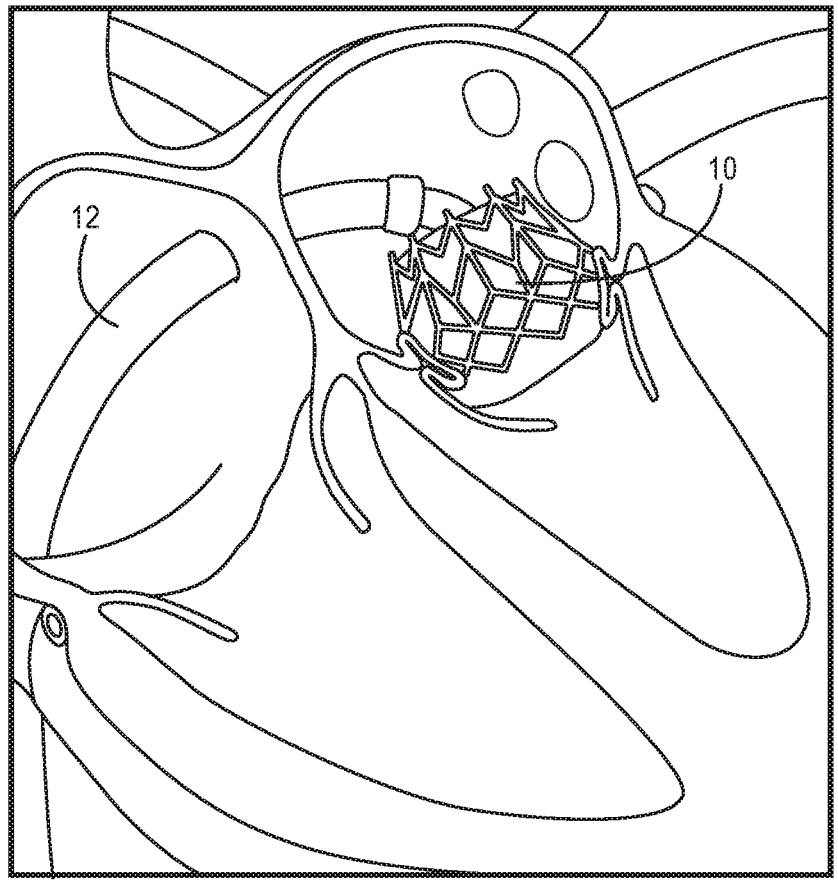
FIG. 1 is a cross-sectional view of a known expandable artificial valve being deployed in a minimally-invasive procedure in a patient's heart.
Figure 2A:
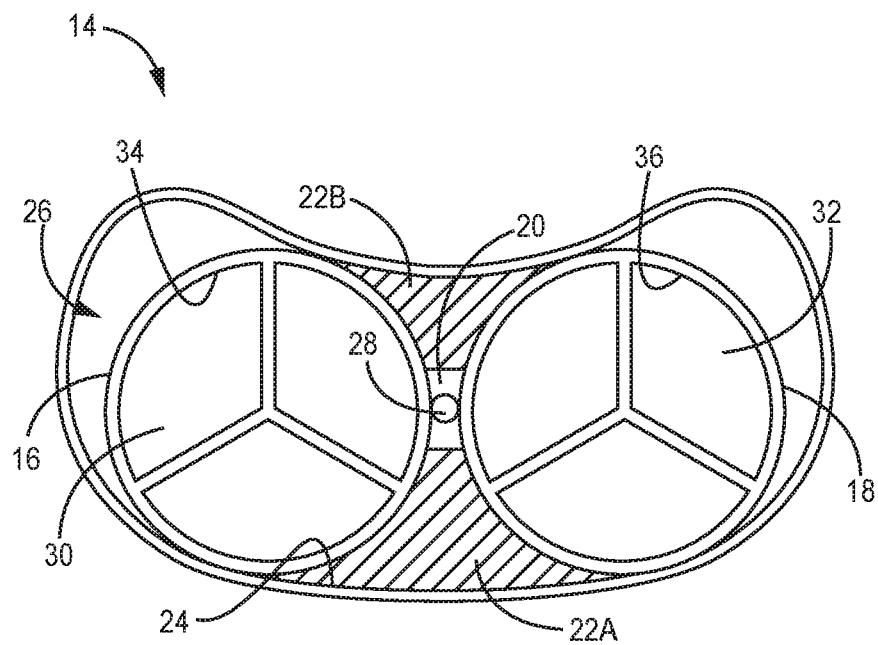
FIG. 2A is a top view of an artificial valve implant, according to one embodiment.
Figure 2B:
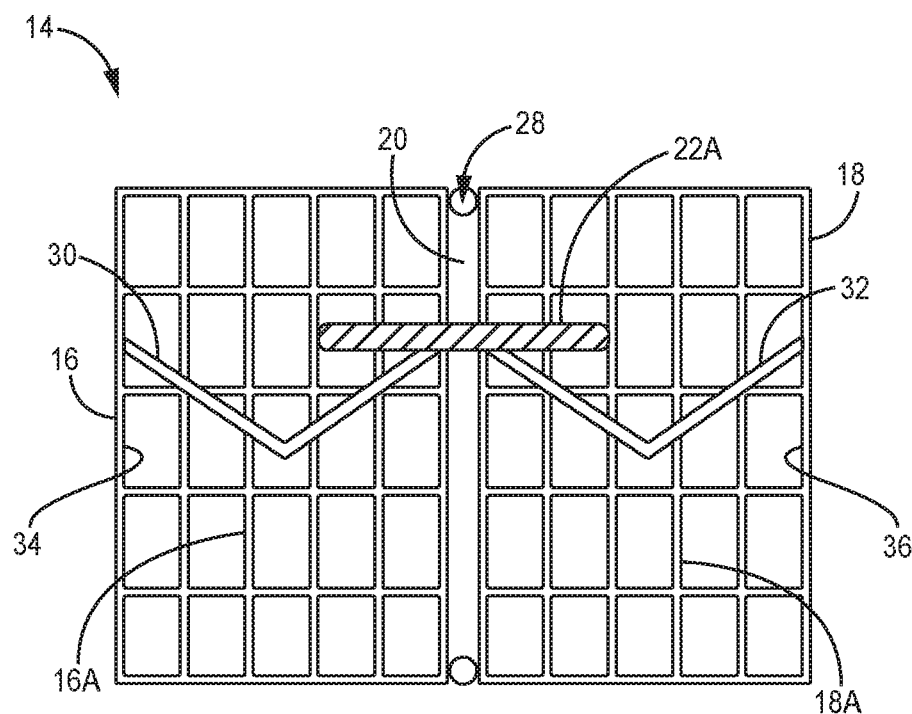
FIG. 2B is a side view of the artificial valve implant of FIG. 2A, according to one embodiment.

FIGS. 2A and 2B depict a mitral valve prosthesis 14, according to one embodiment. More specifically, FIG. 2A depicts a top view of the prosthesis 14 implanted in an annulus 26 of a heart, while FIG. 2B depicts a side view of the prosthesis 14. The prosthesis (also referred to herein as an "implant") 14 has two artificial valves 16, 18 that are coupled with an elongate connection member 20. The connection member 20 is coupled on one side to the first valve 16 and on the other side to the second valve 18, thereby resulting in a dual valve prosthesis 14. Further, the connection member 20 defines a lumen 28 therethrough, which provides for passage of a guidewire (not shown) through the lumen 28 during use. In addition, the prosthesis 14 also has sealing members 22A, 22B sealably attached on each side of the prosthesis 14 to the first and second valves 16, 18 and the connection member 20 as shown such that the sealing members 22A, 22B can provide a seal between the prosthesis 14 and the inner wall 24 of the annulus 26 in which the prosthesis 14 is disposed.

It is understood that each of the first and second valves 16, 18 can have an expandable frame 16A, 18A. Each frame 16A, 18A can be made of expandable metal or shape-memory metal such as, for example, nitinol. For example, in one embodiment, the frames 16A, 18A can be expandable frames that can be inserted into position through a catheter in a retracted or unexpanded configuration and then expanded into an expanded or deployed configuration using balloons as will be described in additional detail below. Alternatively, the frames 16A, 18A can be made of a shape memory material that allows for the frames 16A, 18A to move between an unexpanded, retracted, or undeployed configuration to an expanded or deployed configuration without the need for balloons. In one implementation, the expandable metal frame is substantially similar to the expandable frame of any implantable valve prosthesis having a single valve.

It is further understood that each of the valves 16, 18 have valve leaflets 30, 32 disposed within and attached to the inner surface 34, 36 of each of the valves 16, 18 as shown. The valve leaflets 30, 32 can be, according to one embodiment, made from bovine pericardial tissue or a porcine valve. Alternatively, the valve leaflets 30, 32 can be made from any tissue or material that is used to make any mitral valve leaflet. It is understood that the three valve leaflets 30, 32 as best depicted in FIG. 2A are merely representative of the leaflets in each valve 16, 18. Alternatively, the valves 16, 18 can have any number of leaflets that are known to be included in any known artificial valve.

The sealing members 22A, 22B help to establish a fluidic seal between the inner wall 24 of the annulus 26 and the prosthesis 14, thereby preventing any blood from leaking from one chamber to the next around the outside surfaces or edges of the prosthesis 14 and thus ensuring that all blood flows in the desired direction through the valves 16, 18. In one embodiment, the sealing members 22A, 22B can be made of bovine pericardial tissue or some other type of tissue. Alternatively, the members 22A, 22B can be made of any known material used in artificial mitral valves to establish a fluidic seal. In the implementation as shown in FIGS. 2A and 2B, the prosthesis 14 has one sealing member 22A, 22B on each side. Alternatively, as discussed in further detail below and as shown in FIG. 5, two sealing members 62A, 62B, 64A, 64B can be provided on each side of a prosthesis 60.

Figure 3A:
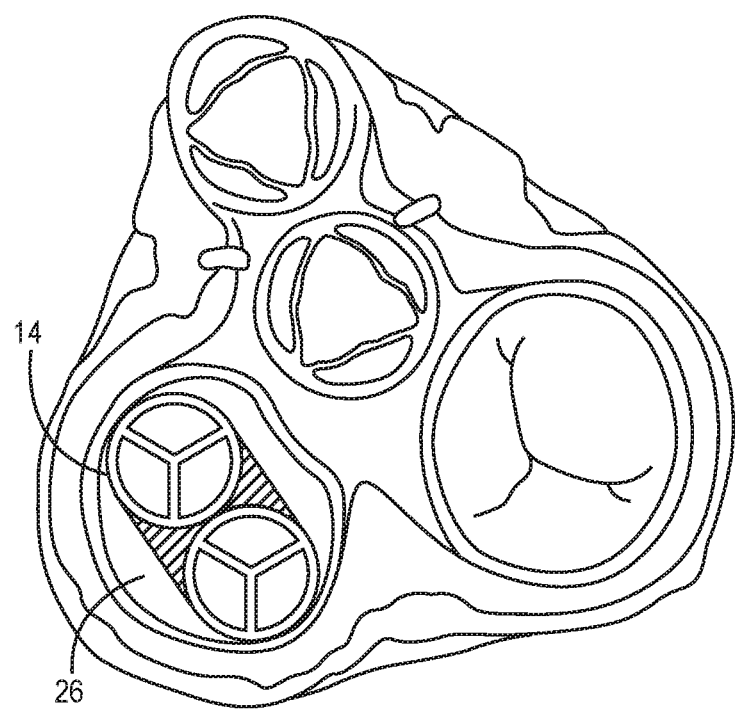
FIG. 3A is a cross-sectional top view of an artificial valve implant being positioned in a patient's heart, according to one embodiment.
Figure 3B:
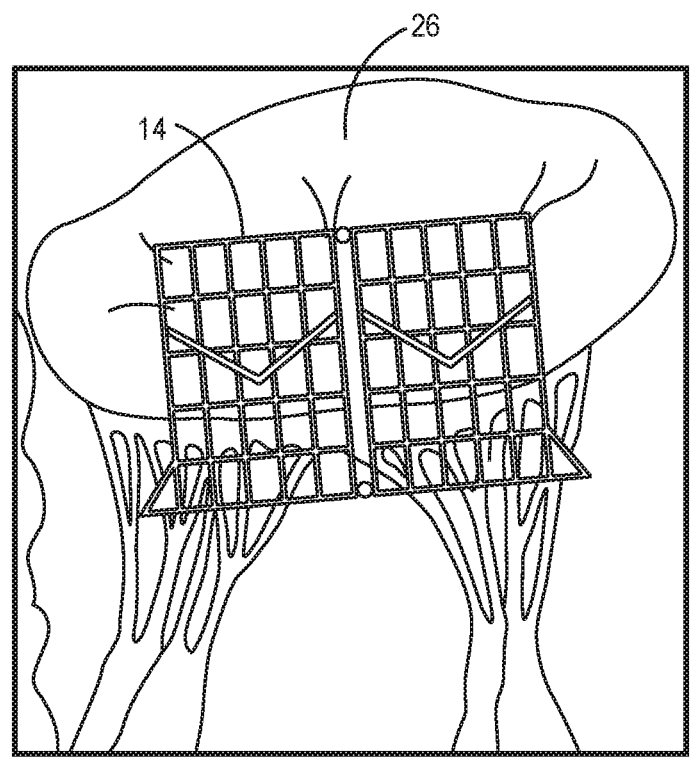
FIG. 3B is a cross-sectional side view of the artificial valve implant of FIG. 3A, according to one embodiment.

In use, the prosthesis 14 can be implanted into the human heart according to any known minimally-invasive procedure, including a catheter-based procedure. For example, FIG. 3A is a cutaway cross-sectional top view of the human heart with the prosthesis 14 positioned in the annulus 26, according to one implementation. Further, FIG. 3B depicts a side view of the same prosthesis 14 in the same annulus 26.

Figure 4:
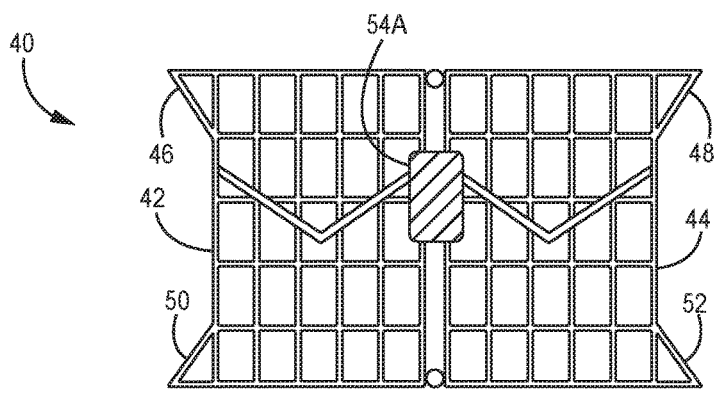
FIG. 4 is a side view of an artificial valve implant, according to another embodiment.

Another embodiment of a dual-valve prosthesis 40 is depicted in FIG. 4. It is understood that this implementation can have similar or identical components or features and alternatives as described above with respect to prosthesis 14 except for the differences discussed herein. This prosthesis 40 has first and second valves 42, 44 with expanded radial rims 46, 48, 50, 52 on each end of each valve 42, 44, with each rim 46, 48, 50, 52 extending radially outwardly away from the central axis of each of the valves 42, 44 such that the rims 46, 48, 50, 52 have a greater diameter than the remainder of each valve body 42, 44, as can be seen in the figure. The rims 46, 48, 50, 52, according to one embodiment, help to seat the prosthesis 40 within the annulus more stably, thereby enhancing retention or attachment of the prosthesis 40 to the inner wall of the annulus. In addition, this prosthesis 40 has sealing members 54A, 54B (with only member 54A being visible in FIG. 4) that are axially thicker than the sealing members 22A, 22B discussed above.

Figure 5:
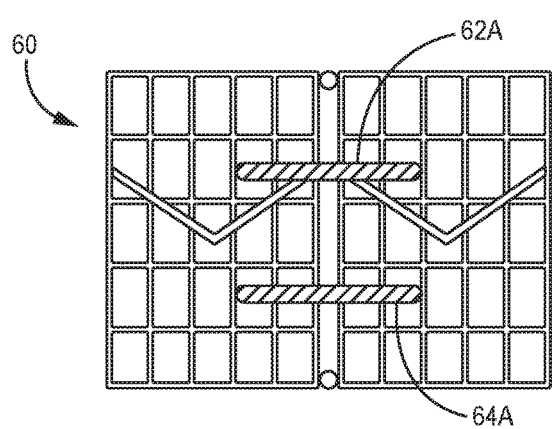
FIG. 5 is a side view of an artificial valve implant, according to yet another embodiment.

A further dual-valve prosthesis 60 is depicted in FIG. 5, according to yet another implementation. It is understood that this implementation can have similar or identical components or features and alternatives as described above with respect to prosthesis 14 and/or prosthesis 40 except for the differences discussed herein. This prosthesis 60 has two upper sealing members 62A, 62B (with only the sealing member 62A visible) and two lower sealing members 64A, 64B (with only the sealing member 64A visible) attached to the sides of the prosthesis 60 in a fashion similar to the sealing member embodiments described above. The two sets of sealing members 62A, 62B, 64A, 64B helps to further strengthen the fluidic seal between the prosthesis 60 and the inner wall of the annulus in which it is positioned by establishing two fluidic seals around the prosthesis 60.

Figure 6:
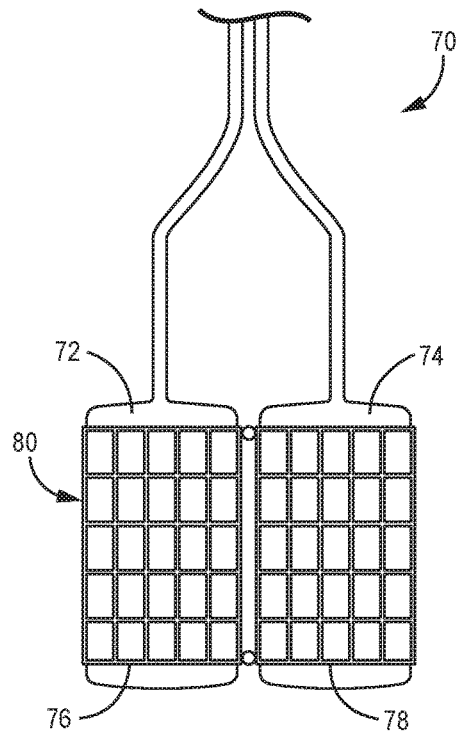
FIG. 6 is a side view of a deployment device for an artificial valve implant, according to another embodiment.

As mentioned above, any of the prosthesis embodiments disclosed or contemplated herein, according to one embodiment, can be deployed using balloons. One example of the deployment balloon device 70 is depicted in FIG. 6, which show first and second balloons 72, 74 disposed within the first and second valves 76, 78 of the prosthesis 80. In use, the balloons 70 are inflated into an inflated position as shown in the figure, thereby urging the prosthesis 80 into its expanding or deployed position.

The various dual-valve prosthesis embodiments disclosed or contemplated herein have some advantages over known mitral valve implants and implantation methods. For example, the dual-valve configuration helps to address the complex structure of the mitral valve annulus in the human heart, thereby helping to establish a better fit and thus a better seal between the prosthesis and the annulus. That is, the profile of the dual-valve prosthesis better fits the annulus into which it is positioned, thereby making the prosthesis easier to position in the annulus, easier to secure, and easier to maintain the fluidic seal.

In addition, the various implementations herein also lower the risk of left ventricular outflow obstruction in comparison to other known transcatheter mitral valve implants. That is, the known single-valve prostheses, due to the circular cross-section of the devices, cause displacement of the anterior mitral leaflet such that the left ventricle outflow tract is compressed into a smaller diameter, thereby increasing the risk of obstruction of that tract. In contrast, the gap in the middle of the prosthesis according to various embodiments herein helps to lower this risk by reducing the displacement of the anterior mitral leaflet, thereby reducing the compression of the outflow tract.

Although the present invention has been described with reference to preferred embodiments, persons skilled in the art will recognize that changes may be made in form and detail without departing from the spirit and scope of the invention.

What is claimed is:

1. A dual-valve prosthesis comprising:
    (a) a first valve structure comprising a first valve disposed therein;
    (b) a second valve structure comprising a second valve disposed therein;
    (c) a connector coupled to the first and second valve structures;
    (d) a first sealing member coupled to the first valve structure, the second valve structure, and the connector on a first side of the prosthesis;
    (e) a second sealing member coupled to the first valve structure, the second valve structure, and the connector on a second side of the prosthesis;
    (f) a third sealing member coupled to the first valve structure, the second valve structure, and the connector on the first side of the prosthesis; and
    (g) a fourth sealing member coupled to the first valve structure, the second valve structure, and the connector on the second side of the prosthesis.

2. The dual-valve prosthesis of claim 1, wherein the connector comprises a lumen defined therethrough.

3. The dual-valve prosthesis of claim 1, wherein the first valve structure is deployable between a first valve retracted position and a first valve deployed position.

4. The dual-valve prosthesis of claim 3, wherein the second valve structure is deployable between a second valve retracted position and a second valve deployed position.

5. A dual-valve prosthesis comprising:
(a) a first valve structure comprising a first valve disposed therein, wherein the first valve comprises three first valve leaflets;
(b) a second valve structure comprising a second valve disposed therein, wherein the second valve comprises three second valve leaflets;
(c) a connector coupled to the first and second valve structures;
(d) a first sealing member coupled to the first valve structure, the second valve structure, and the connector on a first side of the prosthesis; and
(e) a second sealing member coupled to the first valve structure, the second valve structure, and the connector on a second side of the prosthesis.

6. The dual-valve prosthesis of claim 1, wherein the connector is fluidically sealed to the first and second valve structures, and wherein the first and second sealing members are fluidically sealed to the first valve structure, the second valve structure, and the connector.

7. The dual-valve prosthesis of claim 1, wherein the first valve structure is a first expandable frame and the second valve structure is a second expandable frame.

8. The dual-valve prosthesis of claim 1, wherein the first valve structure comprises a first rim at a first end of the first valve structure and a second rim at a second end of the first valve structure, and wherein the second valve structure comprises a third rim at a first end of the second valve structure and a fourth rim at a second end of the second valve structure.

9. A dual-valve prosthesis comprising:
(a) a connector comprising a lumen defined therethrough, wherein the lumen extends along a length of the connector;
(b) a first expandable valve body coupled to a first side of the connector, the first valve body comprising a first valve disposed therein;
(c) a second expandable valve body coupled to a second side of the connector, the second valve body comprising a second valve disposed therein;
(d) a first sealing member coupled to the first valve body, the second valve body, and the connector on a first side of the prosthesis; and
(e) a second sealing member coupled to the first valve body, the second valve body, and the connector on a second side of the prosthesis.

10. The dual-valve prosthesis of claim 9, further comprising:
(a) a third sealing member coupled to the first valve body, the second valve body, and the connector on the first side of the prosthesis, wherein the third sealing member is disposed at a different axial location along the first side of the prosthesis in relation to the first sealing member; and
(e) a fourth sealing member coupled to the first valve body, the second valve body, and the connector on the second side of the prosthesis, wherein the fourth sealing member is disposed at a different axial location along the second side of the prosthesis in relation to the second sealing member.

11. The dual-valve prosthesis of claim 9, wherein the first valve body is deployable between a first valve retracted position and a first valve expanded position and the second valve body is deployable between a second valve retracted position and a second valve expanded position.

12. The dual-valve prosthesis of claim 9, wherein the first valve comprises three first valve leaflets and the second valve comprises three second valve leaflets.

13. The dual-valve prosthesis of claim 9, wherein the connector is fluidically sealed to the first and second valve bodies, and wherein the first and second sealing members are fluidically sealed to the first valve body, the second valve body, and the connector.

14. The dual-valve prosthesis of claim 9, wherein the first valve body is a first expandable frame and the second valve body is a second expandable frame.

15. The dual-valve prosthesis of claim 9, wherein the first valve body comprises a first rim at a first end of the first valve body and a second rim at a second end of the first valve body, and wherein the second valve body comprises a third rim at a first end of the second valve body and a fourth rim at a second end of the second valve body.

16. The dual-valve prosthesis of claim 1, wherein the first valve comprises three first valve leaflets and the second valve comprises three second valve leaflets.

17. The dual-valve prosthesis of claim 5, wherein the connector comprises a lumen defined therethrough.

18. The dual-valve prosthesis of claim 5, wherein the first valve structure is deployable between a first valve retracted position and a first valve deployed position, and wherein the second valve structure is deployable between a second valve retracted position and a second valve deployed position.

19. The dual-valve prosthesis of claim 5, wherein the connector is fluidically sealed to the first and second valve structures, and wherein the first and second sealing members are fluidically sealed to the first valve structure, the second valve structure, and the connector.

20. The dual-valve prosthesis of claim 5, wherein the first valve structure is a first expandable frame and the second valve structure is a second expandable frame.

* * * * *